United States Patent
Wegener et al.

(10) Patent No.: US 6,395,934 B1
(45) Date of Patent: May 28, 2002

(54) RANEY NICKEL CATALYSTS, A METHOD FOR PRODUCING SAID RANEY NICKEL CATALYSTS AND THE USE OF THE SAME FOR HYDROGENATING ORGANIC COMPOUNDS

(75) Inventors: Gerhard Wegener, Mettmann; Eckart Waldau, Düsseldorf, both of (DE); Bernd Pennemann; Bodo Temme, both of League City, TX (US); Hans Warlimont, Dresden; Uta Kühn, Possendorf-Börnchen, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/555,445

(22) PCT Filed: Nov. 20, 1998

(86) PCT No.: PCT/EP98/07457

§ 371 (c)(1),
(2), (4) Date: Jun. 19, 2000

(87) PCT Pub. No.: WO99/28028

PCT Pub. Date: Jun. 10, 1999

(30) Foreign Application Priority Data

Dec. 3, 1997 (DE) .......................................... 197 53 501

(51) Int. Cl.⁷ ............................................. C07C 209/00
(52) U.S. Cl. ........................ 564/422; 502/301; 564/423
(58) Field of Search ........................... 502/301; 564/422, 564/423

(56) References Cited

U.S. PATENT DOCUMENTS

| | | | |
|---|---|---|---|
| 4,287,365 A | 9/1981 | Becker et al. | 564/422 |
| 5,090,997 A | 2/1992 | Birkenstock et al. | 75/338 |

OTHER PUBLICATIONS

Angew. Chem., May 1941, 54, pp. 229–234, Schröter, Neuere Methoden der präparativen Organischen Chemie.

*Primary Examiner*—Samuel Barts
(74) *Attorney, Agent, or Firm*—Joseph C. Gil; Lyndanne M. Whalen

(57) ABSTRACT

Raney nickel catalysts obtainable by a process in which the melt of an alloy comprising 50 to 94 wt. % aluminum, 10 to 50 wt. % nickel, 0 to 20 wt. % iron, 0 to 15 wt. % cerium, cerium mixed metal, vanadium, niobium, tantalum, chromium, molybdenum or manganese and, optionally, further glass-forming elements is allowed to solidify rapidly with a cooling rate of >$10^4$ K/s and the rapidly solidified alloy is then subjected to a treatment with organic or inorganic bases are described.

A process for the preparation of the Raney nickel catalysts mentioned and their use in the hydrogenation of organic compounds, in particular aromatic nitro compounds, are furthermore described.

13 Claims, No Drawings

RANEY NICKEL CATALYSTS, A METHOD FOR PRODUCING SAID RANEY NICKEL CATALYSTS AND THE USE OF THE SAME FOR HYDROGENATING ORGANIC COMPOUNDS

The invention relates to Raney nickel catalysts with an improved service life, a process for their preparation and their use in the hydrogenation of organic compounds, in particular in the hydrogenation of aromatic nitro compounds.

The preparation and use of RaNi as a hydrogenation catalyst for aromatic nitro compounds, such as e.g. nitrobenzene, nitrotoluenes, dinitrotoluenes, chlorinated nitro-aromatics and others, is known and has been described frequently (e.g. R. Schröter, Angew. Chem. 1941, 54, 229, EP-A 0223035). An alloy of aluminium with nickel and, optionally, one or more further sub-group metals is usually used as the starting material for the preparation of RaNi catalysts. The alloy is obtained, for example, by fusion or reactive grinding of the starting metals. RaNi catalysts can be modified in respect of activity, selectivity and stability, in particular at elevated temperatures, by alloying of the starting alloy with other metals. This doping of the catalyst by addition of the most diverse metals to the Al-Ni melt of the catalyst precursors is known (DE-A 40 01 484, DE-A 35 37 247). The catalyst precursors are comminuted by atomizing the Al-Ni metal melt or mechanically and the catalyst is liberated by partial or complete leaching of the aluminium out of the alloy with a base (DE-A 27 13 374). The catalytic action of the catalysts originating from the alloys depends, inter alia, on the qualitative and quantitative composition of the alloy, the structure and the matrix of the alloy and therefore on the resulting structure and the resulting matrix of the catalyst.

Hydrogenation of aromatic nitro compounds is a reaction which is often carried out on a large industrial scale. RaNi catalysts are frequently employed for this. The catalyst service lives, structures and matrix of the starting alloys and the rate of solidification are scarcely correlated. In the ternary systems of Al-Ni-additional metal in particular, a large number of phases can be present in the starting alloy, which show no or only low activities and high catalyst consumptions in the resulting catalyst. The activities and service lives of different catalyst batches are therefore difficult to reproduce.

There was therefore the object of providing RaNi catalysts which show an improved service life and therefore a lower catalyst consumption in the hydrogenation of aromatic nitro compounds.

It has now been found that the service life of RaNi catalysts in the hydrogenation of the nitro groups of aromatic nitro compounds is surprisingly increased compared with the catalysts conventionally employed if, according to the invention, amorphous, partly amorphous or finely crystalline alloys prepared by rapid solidification are employed as precursors for the catalysts.

The invention thus provides RaNi catalysts, which are obtained by a process in which the melt of an alloy comprising 50 to 95 wt. % aluminium, 10 to 50 wt. % nickel and, optionally, 0 to 20 wt. % iron, 0 to 15 wt. % cerium, cerium mixed metal, vanadium, niobium, tantalum, chromium, molybdenum or manganese and, optionally, further glass-forming elements is allowed to solidify rapidly with a cooling rate of $>10^4$ K/s and the rapidly solidified alloy is then subjected to a treatment with organic or inorganic bases.

By quenching a metallic melt at the stated cooling rate, metastable phases and structures outside the state of equilibrium can be obtained and frozen in. A refinement of the matrix, i.e. smaller crystallite sizes, in the range of 1–10 $\mu$m and below, preferably <2 $\mu$m, are established in this way in the catalysts according to the invention. Rapid solidification here is understood as meaning quenching with a cooling rate of $\geq 10^4$ K/s, while the cooling rates with normal atomization which is not according to the invention are between $10^2$ and $10^3$ K/s. If the rapid solidification of the alloy melt takes place at $>10^4$ K/s, amorphous alloys or alloys with crystalline and amorphous regions, called partly amorphous in the following, or completely finely crystalline states are obtained. The term amorphous in connection with metallic phases, also classified as metallic glasses or supercooled solid melts, describes the absence of crystallinity. Surprisingly, it has been found that the RaNi catalysts prepared according to the invention have substantially more stable service lives than those from alloys which have not solidified rapidly.

The high cooling rates of $10^4$ to $10^7$ K/s required for the rapid solidification can be achieved e.g. by forcing an alloy melt out on to a rotating cooling wheel (R. W. Cahn, P. Haasen, E. J. Kramer, Materials Science and Technology vol. 8, 1996, p. 237). Similarly high cooling rates can be obtained by water-in-water atomization of a molten alloy if a correspondingly small particle size is established in the atomization. The particle sizes to be established depend greatly here on the atomization apparatus used, and can easily be determined in a series experiment with which the expert is familiar. Rapidly solidified alloys can also be prepared by the melt extraction process.

The formation of amorphous structures can additionally be influenced in a positive manner by further alloying metals. Rare earth metals, preferably cerium or cerium mixed metal, and/or selected sub-group elements, preferably vanadium, niobium, tantalum, chromium, molybdenum or manganese, are employed as such alloying metals in the catalyst according to the invention. Optionally the alloy can also comprise further glass-forming main group elements, preferably boron, silicon, carbon and/or phosphorus.

The improvement in the catalytic properties effected by rapid solidification is destroyed by annealing the alloys, since the equilibrium states are established again during annealing. The content of amorphous phase in an alloy can be detected by means of X-ray diffractometry and by metallographic examination of ground surfaces of the alloy under a light microscope. (A. Molnar et al., Adv. Catal., 1989, 36, 329).

The catalysts according to the invention based on amorphous/partly amorphous or finely crystalline alloys prepared by rapid solidification are distinguished by increased service lives and low formation of by-products, and by a better reproducibility of the catalyst properties compared with conventional catalysts. The catalyst requirement for use on a large industrial scale is reduced as a result. In the industrial preparation of 2,4-/2,6-tolylenediamine by hydrogenation of dinitrotoluenes or other aromatic nitro compounds for example, this manifests itself advantageously in particular in the hydrogenation in the absence of foreign solvents.

The invention also provides a process for the preparation of RaNi catalysts, in which the melt of an alloy of 50 to 95 wt. % aluminium, 10 to 50 wt. % nickel, 0 to 20 wt. % iron, 0 to 15 wt. % cerium, cerium mixed metal, vanadium, niobium, tantalum, chromium, molybdenum or manganese and, optionally, further glass-forming elements is allowed to cool at a cooling rate of >$10^4$ K/s and the rapidly solidified alloy is then subjected to a treatment with organic or inorganic bases.

Alloys comprising 50 to 95 wt. % aluminium, 10 to 50 wt. % nickel, 0 to 20 wt. % iron and 0 to 15 wt. % cerium, cerium mixed metal, vanadium, niobium, tantalum, chromium, molybdenum or manganese are employed for the preparation according to the invention of the catalysts from rapidly solidified alloys or for the preparation of amorphous, partly amorphous or finely crystalline alloys as catalyst precursors. Alloys of 60 to 90 wt. % aluminium, 15 to 40 wt. % nickel, 0 to 10 wt. % iron and/or other transition metals and 0 to 10 wt. % cerium, cerium mixed metal, vanadium, niobium, tantalum, chromium, molybdenum or manganese are preferred. Alloys of 70 to 85 wt. % aluminium, 15 to 30 wt. % nickel, 0 to 6 wt. % iron and/or other transition metals and 0 to 10 wt. % cerium, cerium mixed metal, vanadium, niobium, chromium, molybdenum or manganese are particularly preferred.

These alloys can be prepared e.g. by inductive smelting of the metals in corresponding weight ratios.

The high cooling rates required for the rapid solidification of the alloys described above can be achieved e.g. by forcing the alloy melt out on to a rotating cooling wheel or into the gap between two cooling wheels rotating in opposite directions, by the melt extraction process or by a water-in-water atomization, with a selected particle size and selected cooling parameters. The atomization of such alloys is known e.g. from DE-A 40 01 484, it being necessary to adhere to the desired cooling rates. The thickness of the bands obtained on the cooling wheels is between 10 and 100 μm, preferably between 10 and 50 μm. The cooling wheel is preferably made of Cu, Ag or Cu- and Ag-based alloys, but can also be produced from any other desired metallic materials. The cooling roll can be cooled with ambient air, cooled and condensed gases, or by water or any other desired cooling medium.

The liberation of the RaNi catalysts is carried out by alkali treatment of the rapidly solidified alloy, which has optionally been comminuted, with aqueous solutions of organic or inorganic bases, for example with sodium hydroxide or potassium hydroxide, sodium carbonate or potassium carbonate, preferably with sodium hydroxide or potassium hydroxide, preferably at temperatures of 50 to 100° C. The amount of base depends on the amount of aluminium present in the alloy. The base can be employed in the stoichiometric amount or more than or less than the stoichiometric amount with respect to the aluminium. A ratio of the amounts of aluminium to base of 1:1 to 1:10 is preferred, and a ratio of 1:1.1 to 1:5 is particularly preferred. The catalyst can be isolated by partial or complete decanting or filtration of the aqueous solution and washed by repeated decanting or filtration of added wash solution. Water (deionized, distilled or drinking water) or a solution of sodium hydroxide or potassium hydroxide in water is used as the wash solution.

The catalysts which can be prepared by leaching out from the rapidly solidified amorphous, partly amorphous or finely crystalline alloys described comprise residual amount of 0 to 15 wt. % aluminium, 50 to 100 wt. % nickel, 0 to 50 wt. % iron and/or other transition metals, and 0 to 30 wt. % cerium, cerium mixed metal, vanadium, niobium, tantalum, chromium, molybdenum or manganese. Catalysts of 0 to 10 wt. % aluminium, 60 to 100 wt. % nickel, 0 to 30 wt. % iron and/or other transition metals and 0 to 30 wt. % cerium, cerium mixed metal, vanadium, niobium, tantalum, chromium, molybdenum or manganese are preferred. Alloys of 0 to 10 wt. % aluminium, 75 to 100 wt. % nickel, 0 to 20 wt. % iron and/or other transition metals and 0 to 25 wt. % cerium, cerium mixed metal, vanadium, niobium, tantalum, chromium, molybdenum or manganese are particularly preferred.

The invention also provides the use of the catalysts described for the hydrogenation of organic compounds, preferably for the hydrogenation of aromatic nitro compounds.

Suitable starting materials for this are any desired aromatic nitro compounds, e.g. nitrobenzene, the isomers and their mixtures of nitrotoluene, chlorinated nitro-aromatics, dinitronaphthalene and, in particular, the isomers and isomer mixtures of dinitrotoluene. The nitro compounds are preferably hydrogenated in bulk, that is to say without the use of a foreign solvent, at temperatures of 120 to 250° C., preferably 140 to 200° C., under a pressure of 5 to 50 bar, preferably 10 to 30 bar, in the presence of the catalyst, which is suspended in the reaction medium. The reaction medium is composed of the product, the water correspondingly formed and the gas phase.

Optionally, a solvent, such as e.g. an alcohol, preferably methanol or 2-propanol, can also be added to the reaction medium for this reaction. The hydrogenation of other nitro compounds is often carried out in a solvent, such as e.g. in an alcohol, preferably in methanol or 2-propanol, under a pressure of 5 to 200 bar.

The hydrogenation can be carried out continuously or discontinuously in the conventional reactors. The amount of nitro compound fed into the reactor here corresponds to the amount of reaction product simultaneously sluiced out of the reactor.

The increase in the service life of the catalysts according to the invention compared with catalysts from conventionally prepared precursor alloys is surprising and unforeseeable. The increase observed in the service life of the catalysts according to the invention can be demonstrated clearly by examples of the reduction of technical grade 2,4/2,6-dinitrotoluene mixtures in the absence of a foreign solvent.

EXAMPLES

Preparation of Alloys

Example 1

Al80Ni20 by Atomization 160 kg aluminium and 40 kg nickel were melted in an induction furnace, heated to 1,300° C. and then poured into a heated ceramic casting gate. The liquid stream of metal of 15 mm diameter emerging from the central bottom discharge was atomized with compressed air of 6.2 bar blown in through a concentrically arranged annular nozzle. The atomized powder was collected in a water tank. The powder was isolated and dried in a stream of hot air.

Example 2

Al80Ni20 by Rapid Solidification

The prealloy was smelted from 800 g aluminium and 200 g nickel in an aluminium oxide crucible in a vacuum induction furnace and poured into a copper mould. Approx. 15 g of these ingots premelted in the form of bars were introduced into the crucible with a fused-on die of a melt spinning unit. Inductive fusion of the prealloy takes place in the course of approx. 2 min with an overheating of approx. 150° C. The melt was forced out through the die by means of argon on to a rotating copper cooling wheel, with an average band thickness of 20 μm.

Example 3

Al80Ni17Fe3 by Rapid Solidification

The rapidly solidified alloy was prepared analogously to example 2 from 800 g aluminium, 170 g nickel and 30 g iron.

Example 4

Annealing of Al80Ni 17Fe3 From Example 3

200 g of a rapidly solidified Al80Ni17Fe3 alloy prepared according to example 3 were annealed for one hour at 600° C. under argon.

Example 5 and 6

Partly Amorphous and Finely Crystalline Al79Ni17Fe3Ce1 by Rapid Solidification The rapidly solidified alloy was prepared analogously to example 2 from 790 g aluminium, 170 g nickel, 30 g iron and 10 g cerium. Each casting (in each case approx. 15 g) from the resulting material was investigated with X-rays. Bands in which an amorphous content was detected were included (approx. 50%) in the partly amorphous batch (example 5), and bands in which no amorphous contents could be detected by X-rays were included in the finely crystalline batch (example 6).

Preparation of a Catalyst 782 g sodium hydroxide were dissolved in 3,129 g water and the temperature of the resulting sodium hydroxide solution was adjusted to 80° C. Under a blanket of nitrogen, 200 g of the comminuted, pulverulent starting alloy were added to the sodium hydroxide solution such that the temperature was kept at 80±2° C. and the foaming was not too severe. The reaction mixture was subsequently stirred at 80° C. for 30 minutes. Thereafter, the supernatant alkali was decanted off and the residue was after-treated with a solution of 78 g sodium hydroxide in 313 g water for 5 minutes, while stirring. This alkali was also decanted, and the catalyst was washed with water to a pH of 8 to 9. The catalyst was obtained quantitatively as an aqueous slurry.

Hydrogenation of DNT

An autoclave of 160 ml volume equipped with a gassing stirrer, a hydrogen feed line, an inlet tube for the nitro compound and an outlet valve for excess hydrogen was used. The reaction mixture left the reactor through a frit, which retained the catalyst. The temperature in the reactor was regulated by an external heating and cooling circulation. A cooling coil inside the reactor ensured additional cooling of the reaction mixture. 180 g of a mixture of a mixture of 80% 2,4-diaminotoluene and 20% 2,6-diaminotoluene (TDA) with water in a weight ratio of TDA to water of 63:37 and 4 g catalyst were initially introduced into the reactor. The contents of the reactor were then placed under pressure with hydrogen and heated up. At a temperature of 180° C. under a pressure of 26 bar, 109 g of a mixture of 80% 2,4-dinitrotoluene and 20% 2,6-dinitrotoluene per hour were passed into the reactor and hydrogenated until the catalyst was spent. The resulting hydrogenation product was removed continuously from the reactor and worked up to give the pure diaminotoluene isomer mixture.

Summary of the results

| Example | Alloy | Structure/preparation | TDA yield % of theory | Service life h |
|---|---|---|---|---|
| 1 | Al80Ni20 | crystalline/air in water atomization | 97.1 | 18 |
| 2 | Al80Ni20 | finely crystalline/rapid solidification on cooling roll | 98.0 | 115 |
| 3 | Al80Ni17Fe3 | finely crystalline/rapid solidification on cooling roll | 97.6 | 128 |
| 4 | Al80Ni17Fe3 | coarsely crystalline/annealing of example 3 | 98.0 | 54 |
| 5 | Al79Ni17Fe3Ce1 | partly amorphous/rapid solidification on cooling roll | 98.0 | 215 |
| 6 | Al79Ni17Fe3Ce1 | finely crystalline/grading from example 5 | 97.8 | 94 |

What is claimed is:

1. A Raney nickel catalyst produced by
    a) rapidly solidifying an alloy melt comprising
        (1) from about 50 to about 90% by weight aluminum,
        (2) from about 10 to about 50% by weight nickel,
        (3) up to about 20% by weight iron,
        (4) up to 15% by weight of cerium, a mixed metal containing cerium, vanadium, niobium, tantalum, chromium, molybdenum or manganese, and optionally,
        (5) glass-forming elements at a cooling rate greater than $10^4$ K/s and
    b) treating the solidified alloy of a) with a base.

2. The catalyst of claim 1 in which at least one element selected from the group consisting of boron, silicon, carbon and phosphorus is present as component (5).

3. The catalyst of claim 2 in which component (5) is present in an amount of up to about 50% by weight in the product of b).

4. A process for the production of a Raney nickel catalyst comprising
    a) rapidly solidifying an alloy melt comprising
        (1) from about 50 to about 90% by weight aluminum,
        (2) from about 10 to about 50% by weight nickel,
        (3) up to about 20% by weight iron,
        (4) up to 15% by weight of cerium, a mixed metal containing cerium, vanadium, niobium, tantalum, chromium, molybdenum or manganese, and optionally,
        (5) glass-forming elements at a cooling rate greater than $10^4$ K/s and
    b) treating the solidified alloy of a) with a base.

5. The process of claim 4 in which step a) comprises forcing the alloy melt on to a rotating cooling wheel.

6. The process of claim 4 in which step a) comprises forcing the alloy melt into a gap between two cooling wheels rotating in opposite directions.

7. The process of claim 4 in which step a) comprises cooling by water-in-water atomization.

8. The process of claim 4 in which step a) comprises cooling by melt extraction.

9. A hydrogenation process comprising reacting an organic compound capable of being hydrogenated with hydrogen in the presence of the catalyst of claim 1.

10. The hydrogenation process of claim 9 in which the organic compound capable of being hydrogenated is a nitroaromatic compound.

11. The hydrogenation process of claim 9 in which the organic compound capable of being hydrogenated is a 2,4–/2,6-dinitrotoluene mixture.

12. A Raney nickel catalyst produced by
    a) rapidly solidifying an alloy melt comprising
       (1) 80% by weight aluminum,
       (2) 17% by weight nickel, and
       (3) 3% by weight iron at a cooling rate greater than $10^4$ K/s and
    b) treating the solidified alloy of a) with a base.

13. A hydrogenation process comprising reacting an organic compound capable of being hydrogenated with hydrogen in the presence of the catalyst of claim 12.

\* \* \* \* \*